United States Patent [19]

Mortensen

[11] 4,212,087
[45] Jul. 15, 1980

[54] PROSTHETIC LEG WITH A HYDRAULIC CONTROL

[76] Inventor: LaVaugh L. Mortensen, 10533 San Anselma Ave., South Gate, Calif. 90280

[21] Appl. No.: 961,114

[22] Filed: Nov. 16, 1978

[51] Int. Cl.² .......................... A61F 1/00; A61F 1/08
[52] U.S. Cl. ............................................. 3/1.2; 3/22; 188/313
[58] Field of Search .................. 3/1.2, 2, 22; 188/313, 188/311, 318

[56] References Cited

U.S. PATENT DOCUMENTS

| | | | |
|---|---|---|---|
| 2,568,051 | 9/1951 | Catranis | 3/1.2 |
| 3,316,558 | 5/1967 | Mortensen | 3/1.2 |
| 3,670,341 | 6/1972 | Webb et al. | 3/1.2 |
| 3,920,253 | 11/1975 | Bauer | 188/313 X |

FOREIGN PATENT DOCUMENTS

| | | | |
|---|---|---|---|
| 316515 | 12/1919 | Fed. Rep. of Germany | 3/1.2 |
| 1811 | of 1907 | United Kingdom | 188/313 |
| 982527 | 2/1965 | United Kingdom | 3/1.2 |

OTHER PUBLICATIONS

"UC-BL Pneumatic Swing-Control Unit for Above-Knee Prostheses" by C. W. Radcliffe et al., Bulletin of Prosthetic Research, Fall, 1960, pp. 73-83, 88 & 89.

*Primary Examiner*—Ronald L. Frinks
*Attorney, Agent, or Firm*—Dominick Nardelli

[57] ABSTRACT

The hydraulic knee control for a prosthetic leg has a cylinder and piston assembly. In addition, within the cylinder is disposed a free floating plug so that the space between the free plug and the head end is filled with air or a compressible fluid, and the spaces between the free plug and the crank end is filled with a liquid or hydraulic fluid. The piston is disposed within this liquid and has sealing means which prevents the liquid from bypassing therearound. Disposed outside of the cylinder are two bypass passageways wherein one end of each passageway communicates with the cylinder in the region between the piston and crank end and the other end of each passageway communicates with the cylinder in the region between the piston and the floating plug. One of the passageways has a one-way adjustable valve which allows the liquid to move only from the head end to the crank end in a controlled manner, and the other passageway has a one-way adjustable valve which allows the liquid to move only from the crank end to the head end in a controlled manner.

9 Claims, 6 Drawing Figures

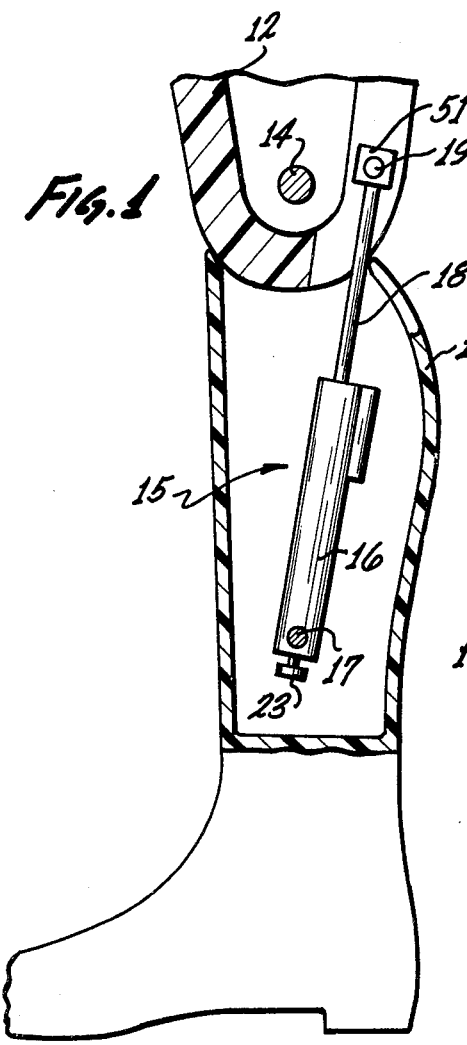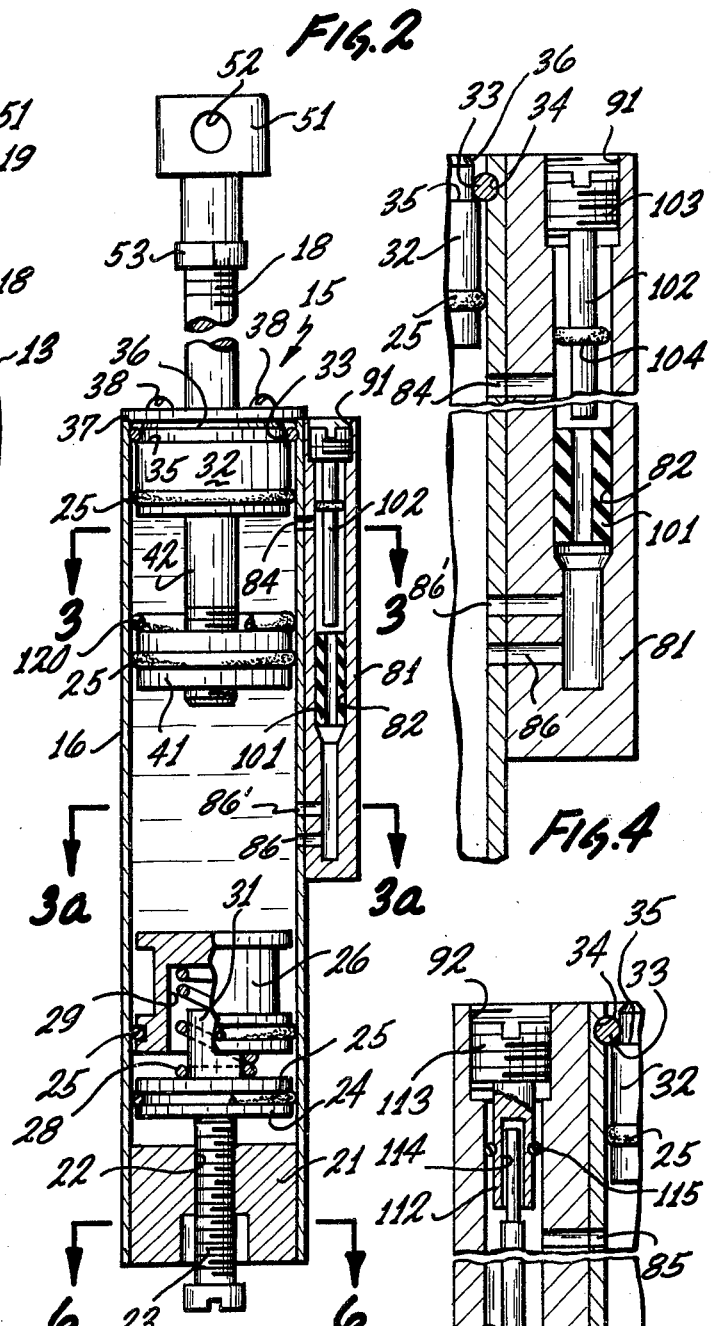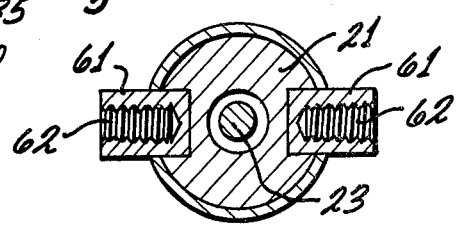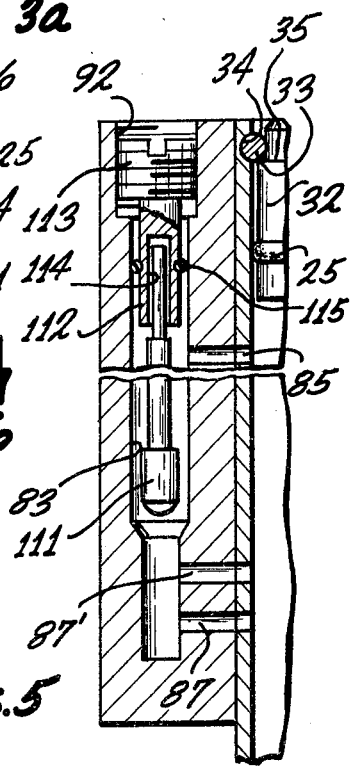

PROSTHETIC LEG WITH A HYDRAULIC CONTROL

FIELD OF THE INVENTION

This invention relates to an artificial leg and, more particularly, to an improved means for controlling the knee action of the leg prosthetic adapted to be used by an above-the-knee amputee.

BACKGROUND OF THE INVENTION

Leg prosthetics are often costly and complex and the motions effected by many devices now in use are awkward and do not closely approximate the natural walking movement. Many of the devices in use include variable controls which are needed by only a small percentage of amputees. In my prior U.S. Pat. No. 3,316,558 I have disclosed a hydraulic knee control which has a compressed air chamber for applying a predetermined pressure on the hydraulic fluid. A piston with a connecting rod moves through the fluid and has an orifice for allowing fluid to bypass therethrough. In addition, a fixed partition is placed within the fluid with an orifice therein which allows fluid to pass therethrough in response to the piston movement to compress or deflate the compressed air. Although this apparatus is an improvement over its prior art devices, the resistance to deflection and knee extension in this device is substantially the same. However, in real life, one knows that knee flexion and knee extension are not usually equal and opposite forces.

OBJECTS OF THE INVENTION

A primary object of this invention is to provide a hydraulic knee control for a leg prosthetic wherein the resistance of flexion is not the same as the resistance to extension.

Another object of this invention is to provide a light, durable, simple, and inexpensive hydraulic knee control for a leg prosthetic.

Another object of this invention is to provide a hydraulic knee control for a leg prosthetic which will enable an amputee to move in a motion that more nearly approaches natural motion.

Another object of this invention is to provide a hydraulic knee control for a leg prosthetic which may be used in conjunction with an independent articulated foot and ankle prosthetic device.

These and other objects and features of advantage will become more apparent after studying the following description of the preferred embodiment of my invention, together with the appended drawing.

BRIEF DESCRIPTION OF THE DRAWING

FIG. 1 is a sectional view of my novel knee control installed in a typical leg prosthetic.

FIG. 2 is an axial sectional view of my novel knee control device removed from the leg prosthetic.

FIG. 3 is a transverse sectional view, taken on line 3—3 of FIG. 2. A sectional view taken on line 3a—3a of FIG. 2 would be substantially the same.

FIG. 4 is a sectional view taken on line 4—4 of FIG. 3 showing a portion of the knee control cylinder.

FIG. 5 is a sectional view taken on line 5—5 of FIG. 3, also showing a portion of the knee control cylinder.

FIG. 6 is a sectional view taken on line 6—6 of FIG. 2 rotated 90 degrees to show the pin assembly mounting ears.

DETAILED DESCRIPTION OF THE DRAWING

Referring to FIG. 1, item 12 indicates a typical lower thigh portion of a leg prosthetic in which a typical lower leg or shank member 13 is hinged by a knee bolt 14 so that the shank portion 13 and the thigh portion 12 pivot relative to each other about bolt 14 in a standard manner. This pivot or knee action is controlled by my novel knee control assembly 15 which has a cylinder 16 pin-connected to the shank portion 13 by a pin assembly 17, and has a connective rod 18 pin-connected to the thigh portion 12 by a pin 19.

Referring to FIG. 2, the assembly 15 is shown in detail and includes the cylinder 16 made of, preferably, thin wall aluminum extruded tubing. At the head end of the cylinder 16, a cylinder head 21 is permanently fixed, for example, by a press-fit. The head 21 has an axially aligned threaded hole 22 into which is threaded a bolt 23. Adjacent to bolt 23 is a moveable plug 24, having sealing means 25 between it and the wall of cylinder 16. Adjacent to the moveable plug is disposed a free floating plug 26 also having sealing means 25 therearound. The moveable plug 24 and the floating plug 26 are urged apart by a suitable compression spring 28, which is nested into a well 29 formed in plug 26 so that the spring 28 is assured of being axially aligned. In addition, plug 24 has a protrusion 31 for reasons that will become apparent hereinafter. The crank end of the cylinder has a sleeve 32 with sealing means 25, and is held in place by a split ring 33 nesting in a groove 34 formed in the internal wall of the cylinder 16. The sleeve 32 has a circumferential shoulder 35 and a circumferential bevel 36 on its axial ends so that after the sleeve is inserted into the cylinder 16 and the split ring is inserted into groove 34, the sleeve is axially moved to the crank end by a method that will be explained hereinafter, the ring 33 is locked into place. Then, an aperture cover plate 37 is suitably bolted to sleeve 32 by screws 38. This action is what causes the split ring to be forced into its respective groove and be locked in place. One understands that, before the sleeve 32 is installed, a piston 41 and connecting rod 42 are first installed in a standard manner. The hole (not shown) in sleeve 32 is threaded over the rod 42. Suitable standard sealing means (also not shown) are provided between the sleeve 32 and rod 42. Sealing means 25 are provided around piston 41 and sleeve 32. All the sealing means 25 are preferably O-ring type seals suitably nested in appropriate grooves, as is standard in the art. The exposed end of rod 18 is threaded onto a suitable dog 51 having a hole 52 for receiving pin 19 (FIG. 1). A locking nut 53 is provided for obvious reasons. The head end contains a means for receiving pin assembly 17 (FIG. 1) which means is comprised of two ears 61 (FIG. 6), each having threaded holes into which are threaded each pin of assembly 17 which pins are preferably two axially aligned bolts threaded into the respective holes 62.

Since the sealing means 25 is disposed around the piston 41, an external bypass appendage 81 is provided to allow the piston 41 to move axially, the appendage 81 has two axially aligned wells 82 and 83, as shown in FIG. 3. Each of these wells communicate with the interior of the cylinder 16 by the aid of apertures 84 and 85, respectively, at the crank end, and by apertures 86 and 87, respectively, at the head end, substantially as shown in FIGS. 4 and 5. At the head end are provided another pair of apertures 86' and 87' axially spaced from 86 and 87, respectively. The purpose of this structure will become apparent hereinafter. The open end of each well 82 and 83 has a threaded counterbore 91 and 92, and at the closed end there is provided a reduced diameter portion into which apertures 86, 86', 87, and 87' communicate. Between the ends thereof there is provided a middle portion with a diameter of a size between the reduced diameter portion and the threaded counterbore. Bypass well 82 controls the rate at which the leg extends itself and well 83 controls the rate at which the leg flexes. This is accomplished as follows: Referring to FIG. 4, there is provided in well 82 an elongated sleeve or tube 101 wherein its outside diameter is such that the sleeve 101 freely moves axially within the well 82 and still prevents fluid from passing between the sleeve and the wall of the well. Into the open end of well 82 is disposed a rod or stem 102 having a head 103 which threads into the counterbore 91. A suitable O-ring seal 104 is provided, as shown. The end of rod 102 extends down into the well 82 so that its end is past aperture 84. Referring to FIG. 5, there is provided in well 83 a floating pin 111 wherein the outside diameter of the portion near the closed end of the well is larger than the diameter of the reduced portion of the well. Into the open end of well 83 is disposed a rod or stem 112 having a head 113 which threads into the counterbore 92. Rod 112 has an axial well 114 opening at its inner end while rod 102 is made solid for reasons that will become apparent hereinafter. Into well 114 is disposed the reduced portion of pin 111 to keep pin 111 in alignment. An O-ring seal 115 is provided around pin 111, as shown.

OPERATION OF THE KNEE CONTROL

The inside of the cylinder 16 is filled with hydraulic oil after the plugs 24 and 26, and spring 28 are installed, as shown. Therefore, any air between the two plugs is trapped therebetween by sealing means 25. The piston 41, rod 42, sleeve 32, split ring 33, and cover 38 are assembled, insuring that the oil is enclosed therein. The knee control is installed into the leg prosthetic, as shown in FIG. 1. When the knee flexes or bends, piston 41 moves down into the cylinder 16 while urging oil out of apertures 86, 86', 87, and 87'. Referring to FIG. 4, as the oil tends to flow into apertures 86 and 86', sleeve 101 is urged against pin 102, blocking any flow of oil. The oil can flow only through bypass well 83 and out of aperture 85 into the other side of piston 41. To control the rate of flow, head 113 is screwed into or out of well 83. Whenever the head 113 is screwed into the well, the rate decreases because the lower or larger end of pin 111 is moved closer to the reduced diameter portion of the well. When the head 113 is screwed out of the well, then obviously the rate of flow increases.

When the leg tends to extend, the piston 41 moves towards the crank end, urging oil out of the apertures 84 and 85. Referring to FIG. 5, when oil is moving from cylinder 16 into the well 83 through aperture 85, pin 111 is urged against the shoulder formed by the reduced portion therein, thereby blocking oil flow therethrough. However, oil flows from cylinder 16 into well 82 through aperture 84 because the sleeve 101 is urged away from pin 102. To control this rate of oil flow, head 103 is screwed into or out of the well 82. Again, when the head 103 is screwed into the well, the rate of flow decreases because the inner end of pin 102 is moved closer to sleeve 101. When the head 103 is screwed out of the well, then obviously the rate of flow increases.

The function of the compressible gas in between plugs 24 and 25 is to provide a static pressure on the hydraulic fluid so as to resiliently resist the inward movement of piston 41, and to assist its outward movement; this resilient pressure helps to control the flexing action of members 12 and 13. The function of the screw 23 is to control the static pressure of the oil therein. This is done with the combination of the air chamber and the spring. The air, being compressible, allows for a large variation of pressures while a liquid, being incompressible, cannot. A resilient O-ring 120 is disposed floating between piston 41 and sleeve 32 to absorb any force between the two members when they come in contact. Apertures 86 and 87 are axially spaced from respective apertures 86' and 87' so that, as hydraulic fluid is inherently lost and screw 23 screwed inward to compensate for this loss of fluid, there is no loss of action when plug 26 has to be moved past the apertures because if one aperture is blocked by the end of plug 26, the other aperture is free.

Having described the preferred embodiment of my invention, one skilled in the art, after studying the description of the preferred embodiment, could devise other embodiments without departing from the spirit of my invention. Therefore, my invention is to be considered as limited only to the scope of the appended claims.

I claim:
1. A leg prosthetic comprising:
an upper thigh member;
a lower shank member;
a knee joint pivotably connecting said members; and
first means pivotably connected between said members for control of said knee joint and comprising:
a cylinder having a head end and a crank end, and pin-connected at said head end to one of said members;
a piston slidably disposed within said cylinder with sealing means therebetween;
a connecting rod connected at one end to said piston and extending out of said crank end, and having the other end thereof pin-connected to the other one of said members;
second means for slidably sealing said crank end around said rod;
a first one-way by-pass valve and a second one-way by-pass valve disposed exterior of said cylinder and each having an inlet port and an outlet port;
said cylinder having a first pair of radial ports and a second pair of radial ports, spaced axially from said first pair;
said inlet port of said first valve and said outlet port of said second valve, each communicating with a respective one of said first pair of radial ports;
said outlet port of said first valve and said inlet port of said second valve each communicating with a respective one of said second pair of radial ports; and
hydraulic fluid disposed within said cylinder.
2. The leg prosthetic of claim 1 wherein said first means further comprises:
means within each one of said one-way valves for controlling the rate of flow of said fluid therethrough as said piston slides axially within said cylinder.
3. The leg prosthetic of claim 2 wherein a floating plug is slidably disposed within said cylinder between said piston and said head end;

sealing means are provided between said floating plug and said cylinder so that a compressible fluid is capable of being contained between said floating plug and said head end;

third means is provided to control the pressure of said compressible fluid.

4. The leg prosthetic of claim 3 wherein said third means comprises:

a moveable plug disposed within said cylinder and between said floating plug and said head end;

sealing means for providing a seal between said moveable plug and said cylinder;

an axially aligned screw threaded through said head end and making contact with said moveable plug so that as the screw is threaded into the cylinder said moveable plug moves axially away from said head end.

5. The leg prosthetic of claim 4 wherein said third means further comprises:

a compression spring disposed between said floating plug and said moveable plug;

said floating plug has a well wherein said spring is disposed;

said moveable plug has a protrusion for nesting within said spring and said well so that minimum volume can be obtained between said plugs.

6. The leg prosthetic of claim 1 wherein said second means comprises:

a sleeve disposed within said cylinder and having said rod protruding therethrough;

sealing means disposed between said sleeve and said rod;

said cylinder having an internal circumferential groove disposed near its crank end;

a split ring nested within said groove so that said sleeve is internal of said ring;

an aperture cover covering the end of said crank end and having screws therein for engaging said sleeve;

said sleeve having an external shoulder near its end adjacent to the crank end, and a bevel formed on the axial end thereof so that, as said screws in said cover are tightened, said bevel forces said ring into said groove and locks the ring in place, and said shoulder bears against said ring to prevent said sleeve from being pulled out of said cylinder and said cover prevents said sleeve from moving into said cylinder.

7. The leg prosthetic of claim 1 wherein said oneway valve includes;

an elongated body having a pair of wells formed therein and each opening at one end of said body;

each of said wells having a bottom portion of a given small diameter, a middle portion of a given median diameter so that a shoulder is formed therebetween and an exposed portion having threads therein;

a stem having a head portion with external threads for coacting with the threads in each of said wells and having a body portion with a diameter smaller than the diameter of said middle portion;

one of said valves has an elongated tube slidably disposed within said middle portion in sealing relationship therewith, and disposed between said stem and said shoulder so that whenever pressure is applied at said outlet port, said tube bears against said stem to prevent fluid flow, and whenever pressure is applied at said inlet, said tube bears against said shoulder to allow fluid to flow;

the other of said valves has an elongated pin slidably disposed within said middle portion and has one end adjacent to said shoulder, which end has a diameter larger than said bottom portion and smaller than said middle portion so that when pressure is applied at said outlet port, said pin bears against said shoulder to prevent fluid flow, and whenever pressure is applied at said inlet port, said pin moves away from said shoulder to allow fluid flow;

both of said stems being capable of being screwed down into said well to restrict fluid flow.

8. The leg prosthetic of claim 4, wherein:

said second means comprises:

a sleeve disposed within said cylinder and having said rod protruding therethrough;

sealing means disposed between said sleeve and said rod;

said cylinder having an internal circumferential groove disposed near its crank end;

a split ring nested within said groove so that said sleeve is internal of said ring;

an aperture cover covering the end of said crank end and having screws therein for engaging said sleeve;

said sleeve having an external shoulder near its end adjacent to the crank end, and a bevel formed on the axial end thereof so that, as said screws in said cover are tightened, said bevel forces said ring into said groove and locks the ring in place, and said shoulder bears against said ring to prevent said sleeve from being pulled out of said cylinder and said cover prevents said sleeve from moving into said cylinder.

9. The leg prosthetic of claim 8, wherein:

each of said one-way valves includes:

an elongated body having a pair of wells formed therein and each opening at one end of said body;

each of said wells having a bottom portion of a given small diameter, a middle portion of a given median diameter so that a shoulder is formed therebetween and an exposed portion having threads therein;

a stem having a head portion with external threads for coacting with the threads in each of said wells and having a body portion with a diameter smaller than the diameter of said middle portion;

one of said valves has an elongated tube slidably disposed within said middle portion in sealing relationship therewith, and disposed between said stem and said shoulder so that whenever pressure is applied at said outlet port, said tube bears against said stem to prevent fluid flow, and whenever pressure is applied at said inlet, said tube bears against said shoulder to allow fluid to flow;

the other of said valves has an elongated pin slidably disposed within said middle portion and has one end adjacent to said shoulder, which end has a diameter larger than said bottom portion and smaller than said middle portion so that when pressure is applied at said outlet port, said pin bears against said shoulder to prevent fluid flow, and whenever pressure is applied at said inlet port, said pin moves away from said shoulder to allow fluid flow;

both of said stems being capable of being screwed down into said well to restrict fluid flow.

* * * * *